United States Patent
Sit et al.

(10) Patent No.: US 6,177,429 B1
(45) Date of Patent: Jan. 23, 2001

(54) DIHYDROPYRAZINE DERIVATIVES AS NPY ANTAGONISTS

(75) Inventors: Sing-Yuen Sit, Meriden; Yazhong Huang, West Haven, both of CT (US)

(73) Assignee: Bristol-Myers Squibb Company, Princeton, NJ (US)

( * ) Notice: Under 35 U.S.C. 154(b), the term of this patent shall be extended for 0 days.

(21) Appl. No.: 09/587,817

(22) Filed: Jun. 6, 2000

Related U.S. Application Data
(60) Provisional application No. 60/140,343, filed on Jun. 21, 1999.

(51) Int. Cl.$^7$ ...................... C07D 401/12; C07D 403/12; A61K 31/497
(52) U.S. Cl. ............................... 514/252.11; 514/255.05; 544/357; 544/406
(58) Field of Search .................................. 544/357, 406; 514/252.11, 255.05

(56) References Cited

U.S. PATENT DOCUMENTS

| | | | |
|---|---|---|---|
| 4,707,486 | 11/1987 | Flockerzi et al. ..................... | 514/318 |
| 4,829,076 | 5/1989 | Szilágyi et al. ....................... | 514/356 |
| 4,912,119 | 3/1990 | Buschauer et al. ................... | 514/333 |
| 5,889,016 | 3/1999 | Bruce et al. .......................... | 544/316 |

FOREIGN PATENT DOCUMENTS

| | | |
|---|---|---|
| 533504 | 3/1993 | (EP) . |
| 534520 | 3/1993 | (EP) . |
| 4049-237 | 6/1990 | (JP) . |
| WO 96-14307 | 5/1996 | (WO) . |

OTHER PUBLICATIONS

C. Chaurasia, et al., "Nonpeptide Peptidomimetic Antagonists of thetide Y Receptor: Benextramine Analogs with Selectivity for the Perifpheral Y$_2$ Receptor", *J. Med. Chem.*, 37 (1994) 2242–2248.

M. B. Doughty, et al., "Neuropeptide Y (NPY) Functional Group Mimetics: Design, Synthesis, and Characterization as NPY Receptor Antagonists", *Bioorganic & Med. Chem. Lett.*, 2 (12) (1992) 1497–1502.

M. B. Doughty, C. S. Chaurasia and K. Li, "Benextramine--NeuropeptidReceptor Interactions: Contributioenzylic Moieties to [$^3$H]Neuropeptide Y Displacement Activity", *J. Med. Chem.*, 36 (1993) 272–279.

Y. Dumont, et al., "Neuropeptide Y and Neuropeptide Y Receptor Subtypes in Brain and Peripheral Tissues", *Progress in Neurobiology*, 38 (1992) 125–167.

L. Edvinsson, M. Adamsson and I. Jansen, "Neuropeptide Y Antagonistic Properties of D–Myl–Inositol–1.2.6–Trisphosphate in Guinea Pig Basilar Arteries", *Neuropeptides*, 17 (1990)99–105.

D. R. Gehlert, "Subtypes of Receptors for Neuropeptide Y: Implications for the Targeting of Therapeutics", *Life Sciences*, 55 (8) (1994) 551–562.

L. Grundemar and R. Håkånson, "Neuropeptide Y and effect on systems: perspectives for drug developement", *TiPS*, 15 (May, 1994) 153–159.

P. A. Hipskind and D. R. Gehlert, "Chapter 1. Neuropeptide Y: At the Dawn of Subtype Selective Antagoinists", *Annual Reports in Medicinal Chemistry*, 31 (1996) 1–10.

J. Lehmann, "Neuropeptide Y: An Overview", *Drug. Dev. Res.*, 19 (1990) 329–351.

J. M. Lundberg, et al., "Recent developments with neuropeptide Y receptor antagonists", *TiPS*, 17 (Sep. 1996) 301–304.

M. C. Michel, "Receptors for neuropeptide Y: multiple subtypes and multiple second messengers", *TiPS*, 12 (Oct., 1991) 389–394.

M. C. Michel and H.J. Motulsky, "He 90481: A Competitive Nonnpeptidergic Antagonist at Neuopeptide Y Receptors", *Annals. of the New York Acad. of Sci.*, 611 (1990) 392–394.

M. C. Michel and A Buschauer, "Neuropeptide Y and its antagonists", *Drugs of the Future*, 17 (1) (1992) 39–45.

K. Rudolf, et al., "The first highly potent and selective non–peptide neuropeptide YY$_1$ receptor antagonist: BIBP3226", *Eur. J. Pharmacology*, 271 (1994) R11–R13.

(List continued on next page.)

*Primary Examiner*—Emily Bernhardt
(74) *Attorney, Agent, or Firm*—Aldo A. Algieri

(57) ABSTRACT

The present invention provides a series of non-peptidergic antagonists of NPY comprising piperidine and piperazine derivatives of 4-phenyl-1,4-dihydropyrazines of the Formula I

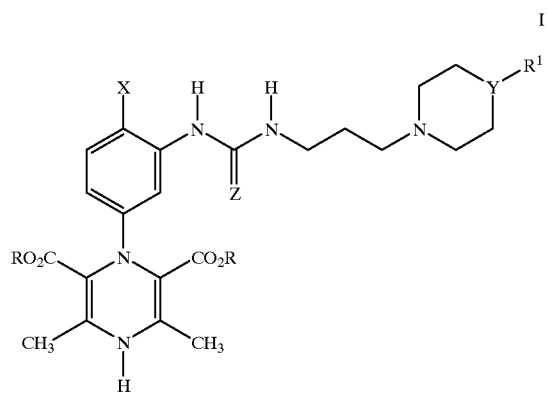

wherein R, R$^1$ X, Y and Z are defined herein. As antagonists of NPY-induced feeding behavior, these compounds are expected to act as effective anorexiant agents in promoting weight loss and treating eating disorders.

7 Claims, No Drawings

OTHER PUBLICATIONS

A. Sahu and S. P. Kaira, "Neuropeptidergic Regulation of Feeding Behavior, Neuropeptide Y", *Trends Endocrinol. Metabolism,* 4 (7) (1993) 217–224.

C. Serradeil–LeGal, et al., "SR120107A and SR120819A: Two Potent and Selective, Orally–Effective Antagonists for NPY $Y_1$ Recptors", *Society for Neuroscience,* Abstract No. 376.14 (1994).

K. Tatemoto, "Neuropeptide Y: Complete amino acid sequence of the brain peptide", *Proc. Natl. Acad. Sci. USA,* 79 (Sep. 1982) 5485–5489.

C. Wahlestedt and D. J. Reis, "Neuropeptide Y–Related Peptides and their Receptors—Are the Receptors Potential Therapeutic Drug Targets?", *Annu. Rev. Pharmacol. Toxicol.,* 32 (1993) 309–352.

M. Frankish, S. Dryden, D. Hopkins, Q. Wang and G. Williams, , "Neuropeptide Y, the Hypothalamus, and Diabetes: Insights into the Central Control of Metabolism", *Peptides,* 16 (4) (1995) 757–771.

J. D. White, "Neuropeptide Y: a central regulator of energy homeostatis", *Regulatory Peptides,* 49 (1993) 93–107.

DIHYDROPYRAZINE DERIVATIVES AS NPY ANTAGONISTS

CROSS REFERENCE TO RELATED APPLICATIONS

This is a nonprovisional application which claims benefit of provisional application U.S. Ser. No. 60/140,343 filed Jun. 21, 1999.

FIELD OF THE INVENTION

The present invention provides novel heterocyclic carbon compounds comprising 4-phenyl-1,4-dihydropyrazines with a piperidinyl or piperazinyl containing moieties attached to the 3-position of the 4-phenyl ring. These compounds act as NPY antagonists.

BACKGROUND OF THE INVENTION

Neuropeptide Y (NPY) is a 36 amino acid peptide first isolated in 1982 from porcine brain [K. Takemoto, *Proc. Nat. Acad. Sci.*, (1982) 79, 5485–5489; D. R. Gehlert, *Life Sciences*, (1994) 55, 551–62; L. Grundemar and R. Håkånson, *TiPS*, (1994) 15, 153–159; J. M. Lundberg, *TiPS*, (1996) 17, 301–304; C. Wahlestedt and D. J. Reis, *Ann. Rev. Pharmacol. Toxicol.*, (1993) 32, 309–352; P. A. Hipskind, *Ann. Rep. Med. Chem.*, (1996), 31, 1–10; J. D. White, *Regulatory Peptides*, (1993) 49, 93–107; A. Sahu and S. P. Kalra, *Trends Endocrinol. Metab.*, (1993) 4, 217–224; Y. Dumont, J.-C. Martel, A. Fournier, S. St. Pierre and R. Quirion, *Prog. Neurobiol.*, (1992) 38,125–167; M. C. Michel and A. Buscher, *Drugs of the Future*, (1992) 17, 39–45; M. C. Michel, *TiPS*, (1991) 12, 389–394; J. Lehmann, *Drug. Dev. Res.*, (1990) 19, 329–351; G. Williams, *Peptides*, (1995) 4, 757–771]. The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neurons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY [L. Grundemar and R. Håkånson, *TiPS*, (1994) 15, 153–159]. These currently include the $Y_1$, $Y_{1-like}$, $Y_2$, $Y_3$, and the $Y_4$ subtypes.

Although specific peptidic antagonists have been identified for most of the subtypes, few selective non-peptidic antagonists have been reported to date. Several competitive but non-selective, non-peptidic antagonists are known. The heterocyclic guanidine derivative He 90481 (4) was found to be a weak but competitive antagonist of NPY-induced $Ca^{++}$ entry in HEL cells ($pA_2$=4.43) [M. C. Michel and H. J. Motulsky, *Annu. Rev. N.Y. Acad. Sci.*, (1990) 611, 392–394; U.S. Pat. No. 4,912,119, 1990 (Heumann Pharma GMBH)]. The compound was also found to have $\alpha_2$-adrenergic and histaminergic activity at this dose range. D-Myo-inositol-1,2,6-triphosphate (5) was reported to be a potent but non-competitive antagonist to NPY-induced contractions in guinea pig basilar artery [L. Edvinsson, M. Adamsson and I. Jansen, *Neuropeptides*, (1990) 17, 99–105]. Similarly, the benextramine-like bisguanidines 6a and 6b were reported to displace $^3$H-NPY in rat brain ($IC_{50}$, 19 and 18.4 $\mu$M) and to display functional antagonism in rat femoral artery [M. B. Doughty, C. Chaurasia and K. Li, *J. Med. Chem.*, (1993) 36, 272–79; M. B. Doughty, S. S. Chu, G. A. Misse and R. Tessel, *BioMed. Chem. Lett.*, (1992) 2, 1497–1502; C. Chaurasia, G. Misse, R. Tessel and M. B. Doughty, *J. Med. Chem.*, (1994) 37, 2242–48]. The bisguanidine 6b was shown to be functionally selective for the $Y_2$ receptor since it antagonized the effect of the $NPY_2$ agonist $NPY_{13-36}$ but had no effect on the vasoconstrictive activity of the $NPY_1$ agonist [Leu31, Pro34]NPY [C. Chaurasia, G. Misse, R. Tessel and M. B. Doughty, *J. Med. Chem.*, (1994) 37, 2242–48].

A substantial body of art has accumulated over the past two decades with respect to 4-aryl-1,4-dihydropyridine compounds. A large number of these possess calcium antagonist properties and find utility in the treatment of cardiovascular diseases. Several 4-aryl-1,4-dihydropyridines with piperidine-ring-containing-substituents have been reported.

A series of compounds of formula (1) was claimed to be

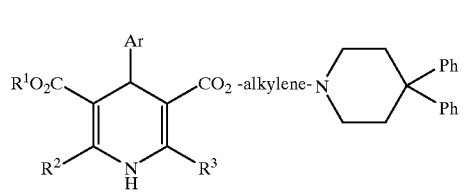

useful as vasodilators, antihypertensives and diuretics by Flockerzi, et al., in U.S. Pat. No. 4,707,486, issued Nov. 17, 1987.

A series of dihydropyridines, including compounds of formula (2), were disclosed and claimed to have antitumor promoting activity in European Patent Application 533,504, published on Mar. 24, 1993.

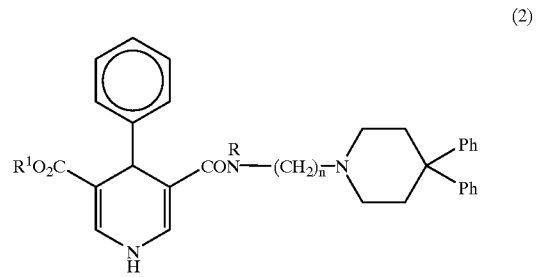

European Patent Application 534,520, published on Mar. 31, 1993, discloses related compounds having formula (3) wherein $R^5$ is alkyl, phenyl and aralkyl.

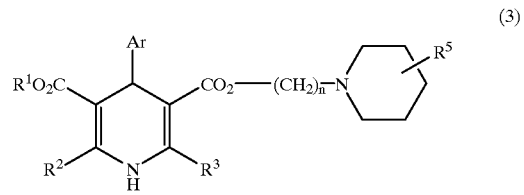

A compound of formula (4) has been disclosed in JO 4049-237-A, published on Jun. 15, 1990, and claimed to be an inhibitor of Phospholipase A$_2$.

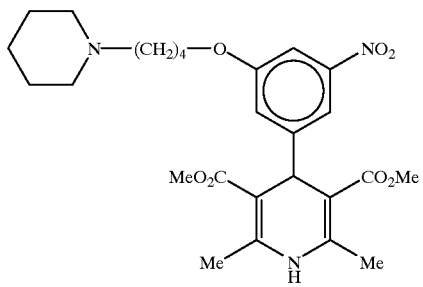

(4)

Of less significance is a series of antihypertensive dihydropyridine anilide derivatives disclosed by Szilagyi, et al, in U.S. Pat. No. 4,829,076, issued May 9, 1989, and containing compounds of formula (5)

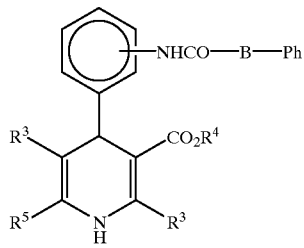

(5)

in which B is a chemical bond or an alkylene group.

A guanidine derivative of formula (6) having NPY-Y$_1$ selective receptor antagonist activity was

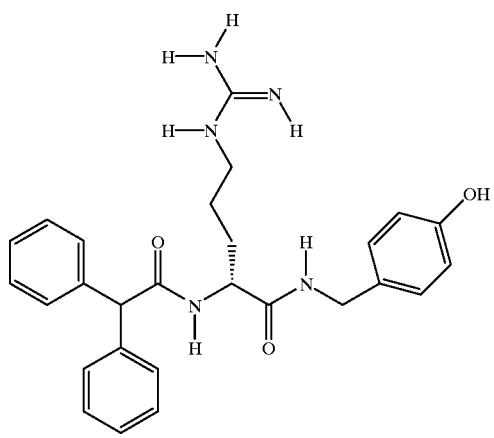

(6)

disclosed by Rudolf, et al. *Eur. J. Pharmacology*, (1994) 271, R11–13.

A series of substituted benzylamine derivatives of the general formula (7) having NPY-Y$_1$ receptor antagonist activity

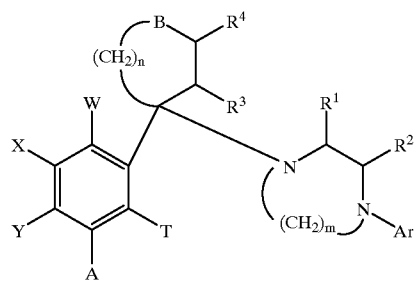

(7)

was disclosed by Peterson, et al. in International Patent Application WO 96/14307, published May 17, 1996.

A series of 4-phenyl-1,4-dihydropyrimidinones derivatives of the general formula (8) having NPY-Y$_1$ receptor antagonist activity

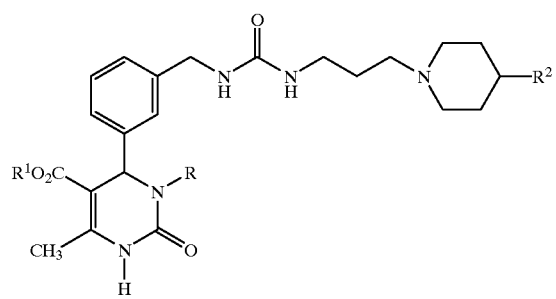

(8)

was disclosed by Bruce, et al, in U.S. Pat. No. 5,889,016, issued on Mar. 30, 1999, and claimed to promote weight loss and treatment of eating disorders.

These reference compounds are readily distinguished structurally from the compounds of the instant invention by virtue of many of the art compounds having the piperidine substituents attached to the dihydropyridine ring itself or to a phenyl ring which is attached to a dihydropyridine ring or a dihydropyrimidone ring. In contrast, compounds of the instant invention contain piperidine or piperazine moieties attached to the 3-position of the 4-phenyl ring which is then attached to a dihydropyrazine ring. Not only are the present compounds structurally novel, they also have been discovered to possess novel NPY antagonist activity.

In summary, the prior art does not disclose nor suggest the unique combination of structural fragments which embody these novel dihydropyrazine derivatives as having good antagonist activity at NPY-Y$_1$ receptor sites.

SUMMARY AND DETAILED DESCRIPTION OF THE INVENTION

The present invention comprises the compounds of Formula I,

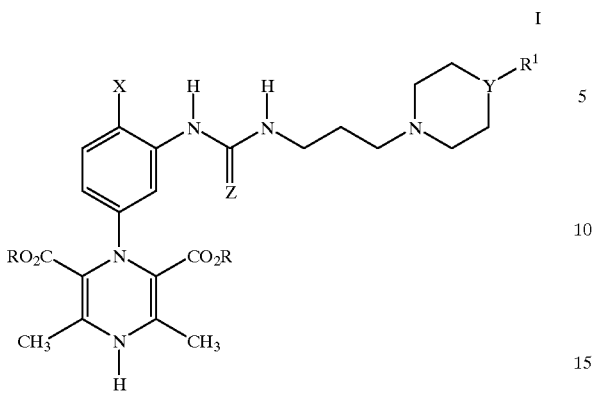

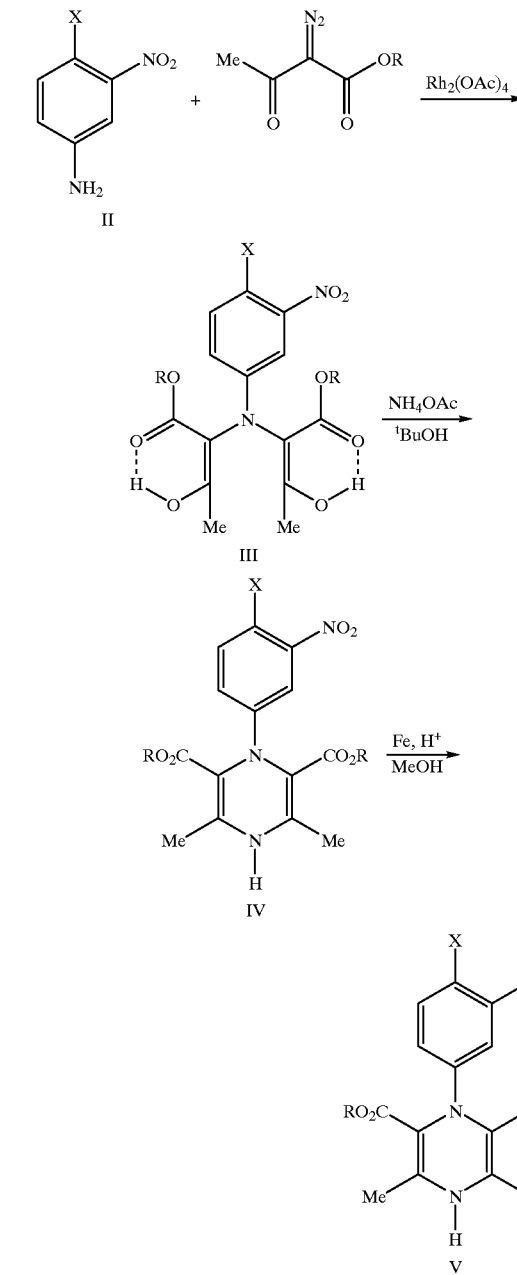

Reaction Scheme 1

The term "$C_{1-3}$ alkyl" indicates that the alkyl group contains from one to three carbon atoms, such as methyl, ethyl, propyl and isopropyl. Preferred compounds of the instant invention are Formula I compounds wherein R is methyl and Z is N—CN or O. Most preferred compounds are those wherein Y is CH, X is hydrogen and $R^1$ is selected from substituted phenyl, particularly with methoxy substituents.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicylic acid, phthalic acid, enanthic acid, and the like.

The Formula I compounds can also be quaternized by standard techniques to yield quaternary piperazinium salt products of Formula I. Quaternization would be expected to maximize the peripheral effects of Formula I compounds and minimize brain penetration.

The compounds of the present invention may be prepared by various procedures such as those illustrated herein in the examples, in the reaction schemes and variations thereof which would be evident to those skilled in the art. The various compounds of Formula I may advantageously be prepared from the dihydropyrazine intermediates of Formula V wherein X is hydrogen or fluoro as illustrated in Reaction Schemes 2 and 3.

The various dihydropyrazine intermediates are generally prepared from the intermediates of the general Formula III as illustrated in Reaction Scheme 1.

It will be appreciated by those skilled in the art that the core 1,4-dihydro-4-phenyl-2,6-dimethyl-3,5-pyrazinedicarboxylic acid in Formula IV may be prepared from a nitro aniline of Formula II with a rhoduim catalyzed N-alkylation by diazo acetate. Advantageously, the aniline group of Formula II is alkylated by diazo acetoacetate in the presence of a catalytic amount and, preferably with 0.2 to 0.4 mol % of rhodium acetate dimer to produce the bis-alkylated aniline intermediate of Formula III. The resulting bis-alkylated intermediate is then readily cyclized with ammonium acetate and preferably the transformation is carried out in tert-butanol to minimize undesired side reactions. The nitro group of the Formula IV compound may readily be reduced with iron under acidic conditions in an alcohol solvent to provide the core dihydropyrazine intermediate of Formula V wherein X is hydrogen or fluoro.

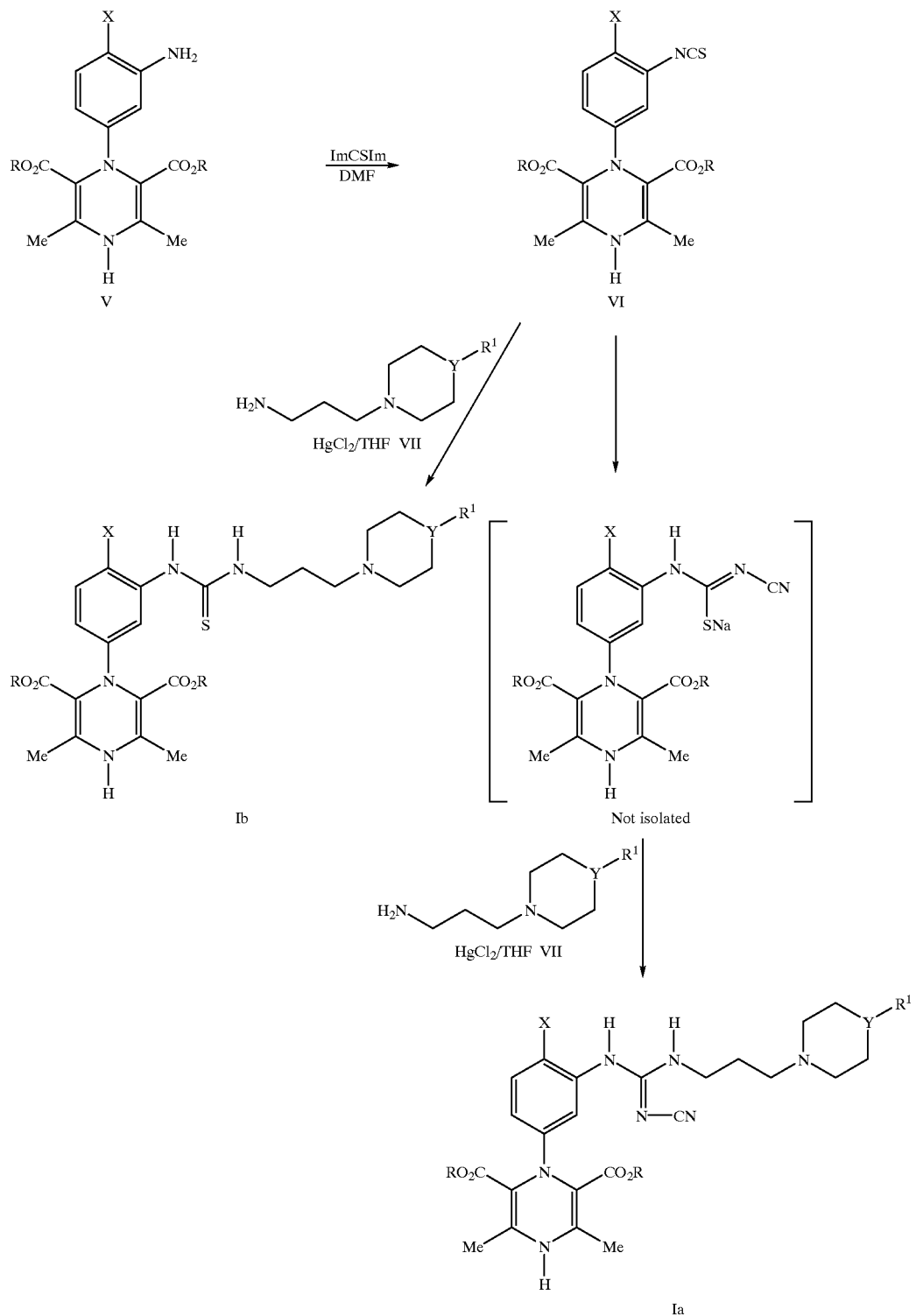

Reaction Scheme 2

The compounds of Formula I may be prepared from the intermediates of Formula V as outlined by the processes illustrated in Reaction Schemes 2 and 3. In Reaction Scheme 2, the amino group on the phenyl dihydropyrazine intermediate of Formula V is reacted with thiocarbonyldiimidazole in dimethylformamide to produce the isothiocyanate intermediate of Formula VI which is then advantageously used to prepare the cyanoguanidines of Formula Ia or thioureas of Formula Ib. The compounds of Formula Ia can be prepared by treating the compound of Formula VI with sodium cyanamide in an alcoholic solvent and then reacting the resulting intermediate with the desired piperidinyl or piperazinyl propanamine of Formula VII in the presence of mercuric chloride to provide the corresponding dihydropyrazine cyanoquanidines of Formula Ia. It should be appreciated by those skilled in the art that the thiocyanate intermediate of Formula VI can also be treated with the desired piperidinyl or piperazinyl propanamine to provide the corresponding dihydropyrazine thioureas of Formula Ib.

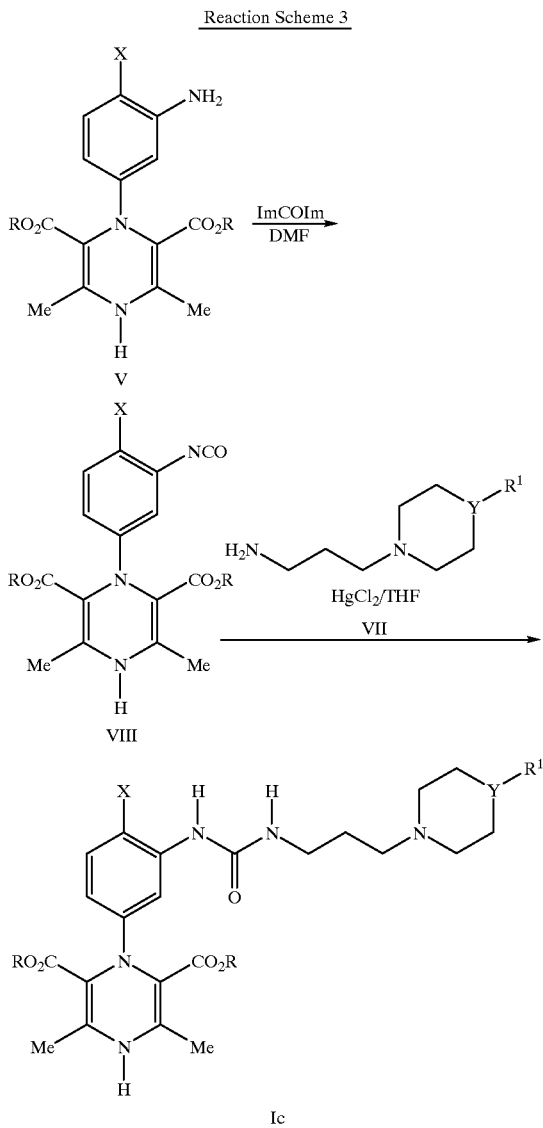

Reaction Scheme 3

When it is desired to prepare the compounds of Formula Ic, the aminophenyl dihydropyrazine intermediates of Formula V is reacted with carbonyldiimidazole in dimethylformamide to provide the isocyanate intermediate of Formula VIII which is then treated with the desired piperidinyl or piperazinyl propanamine of Formula VII to produce the corresponding urea compounds of Formula Ic.

Additional reactions intermediates and Formula I products can be prepared by appropriate modification of the foregoing synthetic schemes and procedures. Such modifications would be obvious to those skilled in the art.

The compounds of this invention demonstrate binding affinity at NPY-$Y_1$ receptors. This pharmacologic activity is assayed in SK-N-MC (human neuroblastoma) cell membranes using iodine-125-labeled I-PYY as a radioligand. The compounds of this invention had good binding affinities as evidenced by $IC_{50}$ values being about 1 μM or less at NPY-$Y_1$ receptors. Preferred compounds have $IC_{50}$ values less than 500 nM.

Although as a class, these types of compounds have significant affinity for $\alpha_1$-adrenergic receptors and/or $Ca^{++}$ channels, the compounds of this invention possess much weaker affinities for $\alpha_1$ adrenergic receptors and $Ca^{++}$ channels. Pharmacologically, these compounds act as selective NPY antagonists at NPY-$Y_1$ receptor sites. As such, the compounds of Formula (I) are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula (I) or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal track;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and disorders, such as male erectile dysfunction and benign prostatic hyperplasia, and reproductive disorders;

conditions or disorders associated with inflammation;

respiratory diseases, such as asthma and conditions related to asthma and bronchoconstriction;

diseases related to abnormal homone release, such as leutinizing hormone, growth hormone, insulin and prolactin; and sleep disturbance and diabetes.

There is evidence that NPY contributes to certain symptoms in these disorders: hypertension, eating disorders, and depression/anxiety [C. Wahlestedt and D. J. Reis, *Annual Rev. Pharmacol. Toxicol.*, (1993) 32, 309–52; p. 331]; as well as circadian rhythms. Compounds of this invention are expected to be useful in treating these disorders as well as sleep disturbance and diabetes.

These compounds are expected to block NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat hypertension, depression, diabetes and anxiety disorders.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope.

In the following examples, all temperatures are given in degrees Centigrade. Melting points were recorded on a Gallenkamp capillary melting point apparatus are uncorrected. Proton magnetic resonance ($^1$H NMR) spectra and carbon magnetic resonance ($^{13}$C NMR) spectra were recorded on a Bruker AC 300 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular weight (MH$^+$) or (M-H)$^-$ was determined on a Finnigan TSQ 7000. The element analyses are reported as percent by weight.

GENERAL METHOD FOR THE PREPARATION OF INTERMEDIATES

Preparation 1

2,2'-[N-(3-Nitrophenyl)imino]bis(1,3-propanedioic acid), tetramethyl ester

A mixture of 3-nitroaniline (3.6 mmol), rhodium acetate dimer (0.0086 mmol) and 10 mL of dry benzene was warmed to reflux. To this was added a solution of methyl α-acetyl-α-diazoacetate [described by J. C. Lee, *Syn. Comm.*, Vol. 25(7), p. 1511 (1995)] (13.0 mmol) in benzene (10 mL) dropwise over a period of 2 hours. The resulting mixture was refluxed until all the diazoacetate was consumed. After cooling to room temperature, the volatiles were removed in vacuo and the residue was filtered over silica gel, eluted with 20% (v/v) ethyl acetate in hexanes. The crude material obtained from the filtration was subjected to further crystallization to give the title compound as orange crystals (0.95 mmol, 26.3%): mp 146–147° C.; $^1$H-NMR (CDCl$_3$) δ 12.76 (s, 1H), 12.73 (s, 1H), 7.56 (dd, 1 H, J=8.2, 2.0 Hz), 7.41 (t, 1H, J=2.2 Hz), 7.31 (t, 1 H, J=8.2 Hz), 6.92 (dd, 1H, J=8.2, 2.4 Hz), 3.74 (s, 6H), and 1.84 (s, 6H); $^{13}$C-NMR (CDCl$_3$) δ 177.1, 172.4, 149.9, 130.2, 120.0, 113.3, 108.3, 52.0, and 19.6.

Anal. Calcd. for C$_{16}$H$_{18}$N$_2$O$_8$: C, 52.46; H, 4.95; N, 7.65. Found: C, 52.31; H, 4.95; N, 7.65.

Preparation 2
2.2'-[N-(3-Nitro-4-fluorophenyl)imino]bis(1,3-propanedioic acid), tetramethyl ester The title compound was prepared from 4-fluoro-3-nitroaniline using the general procedure described in Preparation 1 to afford the product as orange crystals: mp 161–163° C.; $^1$H-NMR (CDCl$_3$) δ 12.73 (s, 2H), 7.19 (dd, 1H, J=5.9, 3.2 Hz), 7.10 (t, 1H, J=9.5 Hz), 6.86 (dt, 1H, J$_d$=9.2 Hz, J$_t$=3.6 Hz), 3.75 (s, 6H), and 1.87 (s, 6H); $^{13}$C-NMR (CDCl$_3$) δ 177.1, 172.3, 150.0, 146.6, 145.6, 120.0 (d, J$_F$=7.1 Hz), 119.3 (d, J$_F$=22.2 Hz), 109.7, 107.1, 52.0, and 19.6.

Anal. Calcd. for C$_{16}$H$_{17}$FN$_2$O$_8$: C, 50.00; H, 4.46; N, 7.29. Found: C, 50.21; H, 4.56; N, 7.28.

Preparation 3
1,4-Dihydro-2,6-dimethyl-4-(3-nitrophenyl)-3,5-pyrazinedicarboxylic acid, dimethyl ester 2,2'-[N-(3-Nitrophenyl)imino]bis(1,3-propanedioic acid), tetramethyl ester (3.1 mmol) was refluxed with ammonium acetate (290 mg) in tert-butanol (30 mL) and the reaction was completed in less than 0.5 hours. After chromatography (Silica gel, 40% (v/v) ethyl acetate in hexanes), 750 mg of the title compound was isolated as an orange foam (yield 69%); $^1$H-NMR (CDCl$_3$) δ 7.66 (dd, 1H, J=8.2,1.4 Hz), 7.47 (t, 1H, J=2.3 Hz), 7.26 (t, 1H, J=8.2 Hz), 6.95 (dd, 1H, J=8.2, 2.5 Hz), 6.21 (s, 1H), 3.78 (s, 6H), and 2.45 (s, 6H); $^{13}$C-NMR (CDCl$_3$) δ 165.6, 151.5, 149.5, 148.9, 129.3, 119.1, 114.6, 108.6, 108.1, 52.0, and 18.1.

Anal. Calcd. for C$_{16}$H$_{17}$N$_3$O$_6$·0.25H$_2$O: C, 54.62; H, 5.01; N, 11.94. Found: C, 54.83; H, 5.22; N, 11.39.

Preparation 4
1,4-Dihydro-2,6-dimethyl-4-(3-nitro-4-fluorophenyl)-3,5-pyrazinedi-carboxylic acid, dimethyl ester The title compound was prepared from 2,2'-[N-(3-nitro-4-fluorophenyl)imino]bis(1,3-propanedioic acid), tetramethyl ester using the procedure described in Preparation 3 to afford the desired product as an orange foam (yield 50%); $^1$H-NMR (CDCl$_3$) δ 7.19 (dd, 1H, J=5.9, 3.2 Hz), 7.10 (t, 1H, J=9.5 Hz), 6.86 (dt, 1H, J$_d$=9.2 Hz, J$_t$=3.6 Hz), 3.75 (s, 6H), and 1.87 (s, 6H); $^{13}$C-NMR (CDCl$_3$) δ 165.5, 151.2, 149.7, 148.0, 147.1, 120.0 (d, J$_F$=7.1 Hz), 118.2 (d, J$_F$=22.2 Hz), 109.9, 108.7, 52.0, and 18.1.

Anal. Calcd. for C$_{16}$H$_{16}$FN$_3$O$_6$·0.35EtOAc·0.67H$_2$O: C, 51.20; H, 4.97; N, 10.29. Found: C, 51.19; H, 4.69; N, 10.29.

Preparation 5
4-(3-Aminophenyl)-1,4-dihydro-2,6-dimethyl-3,5-pyrazinedicarboxylic acid, dimethyl ester 1,4-Dihydro-2,6-dimethyl-4-(3-nitrophenyl)-3,5-pyrazinedi-carboxylic acid, dimethyl ester (219 mg, 0.63 mmol) was dissolved in 30 mL methanol containing 3 mL of water in a flask equipped with a mechanical stirrer. Iron powder (300 mg) was added, followed by one drop of 37% hydrochloric acid. The whole mixture was refluxed moderately with mechanical stirring for 3.5 hours. Usual extractive work up furnished the title compound as yellow solid (176 mg, 88%): mp 212–213° C.; $^1$H-NMR (CDCl$_3$) δ 6.91 (t, 1H, J=8.0 Hz), 6.20 (dd, 1H, J=7.8, 2.0 Hz), 6.11 (dd, 1H, J=8.2, 2.3 Hz), 6.00 (t, 1H, J=2.2 Hz), 5.93 (s, 1H), 3.77 (s, 6H), and 2.38 (s, 6H); $^{13}$C-NMR (CDCl$_3$) δ 166.8, 152.0, 148.5, 146.9, 129.6, 109.5, 107.8, 104.2, 100.3, 51.8, and 17.9.

Anal. Calcd. for C$_{16}$H$_{19}$N$_3$O$_4$: C, 60.56; H, 6.04; N, 13.24. Found: C, 60.05; H, 6.14; N, 12.66.

Preparation 6
1,4-Dihydro-2,6-dimethyl-4-(3-isothiocyanatophenyl)-3,5-pyrazinedicarboxylic acid, dimethyl ester 4-(3-Aminophenyl)-1,4-dihydro-2,6-dimethyl-3,5-pyrazinedicarboxylic acid, dimethyl ester (3.8 mmol) in 16 mL of DMF was slowly added into a DMF solution (20 mL) of 1,1'-thiocarbonyldiimidazole (5.2 mmol) and the reaction went to completion in 0.5 hours. After DMF was removed in vacuo, the residue was purified by chromatography on silica gel eluted with 50% (v/v) ethyl acetate in hexanes to give the title compound as a yellow powder (1.19 g, 87%); $^1$H-NMR (CDCl$_3$) δ 7.09 (t, 1H, J=8.1 Hz), 6.73 (dd, 1H, J=7.8, 1.9 Hz), 6.59 (dd, 1H, J=8.3, 2.4 Hz), 6.47 (t, 1H, J=2.1 Hz), 6.06 (s, 1H), 3.79 (s, 6H), and 2.43 (s, 6H); $^{13}$C-NMR (CDCl$_3$) δ 166.0, 151.7, 149.1, 131.3, 129.6, 117.7, 112.6, 110.3, 108.9, 52.0, and 18.1.

Anal. Calcd. for C$_{17}$H$_{17}$N$_3$O$_4$S·0.2H$_2$O: C, 56.25; H, 4.83; N, 11.58. Found: C, 56.28; H, 4.96; N, 11.11.

EXAMPLE 1
4-[3-[[(Cyanoimino)[[3-(4-phenyl-1-piperidinyl)propyl]-amino]methyl]amino]phenyl]-1,4-dihydro-2,6-dimethyl-3,5-pyrazinedicarboxylic acid, dimethyl ester 1,4-Dihydro-2,6-dimethyl-4-(3-isothiocyanatophenyl)-3,5-pyrazinedicarboxylic acid, dimethyl ester (144 mg, 0.40 mmol) was added into sodium cyanamide (28 mg, 0.44 mmol) in 3 mL of EtOH and the mixture was stirred for 20 minutes. EtOH was then removed in vacuo and the resultant foam-like material was mixed with 4-phenyl-piperidine-1-propanamine (105 mg, 0.48 mmol) in 5 mL of THF. The mixture was cooled down to 0° C. and HgCl$_2$ (109 mg) was added. The reaction was completed in 15 min. After filtration and extraction, the organic layer was concentrated and purified by chromatography (silica gel, eluted with 10% (v/v) methanol in methylene chloride) to yield the title compound as isolated as a yellow foam (175 mg, 75%); $^1$H-NMR (CDCl$_3$) δ 7.05–7.35 (m, 6H), 6.75 (br, 1H), 6.65 (d, 1H, J=7.5 Hz), 6.58 (d, 1H, J=8.3 Hz), 6.53 (br, 1H), 5.98 (br, 1H), 3.72 (s, 6H), 3.38 (m, 2H), 2.97 (m, 2H), 2.30–2.55 (m, 3H), 2.39 (s, 6H), 2.03 (m, 2H), 1.65–1.80 (m, 4H), 1.40–1.60 (m, 2H); $^{13}$C-NMR (CDCl$_3$) δ 166.2, 152.6, 149.4, 129.9, 128.5, 126.9, 126.3, 118.3, 116.3, 112.5, 110.4, 108.7, 54.1, 51.8, 42.4, 41.0, 32.7, 29.8, 25.6, and 17.9.

Anal. Calcd. for C$_{32}$H$_{39}$N$_7$O$_4$·0.7CH$_2$Cl$_2$·0.24H$_2$O: C, 60.48; H, 6.34; N, 15.10. Found: C, 60.59; H, 6.71; N, 14.45.

EXAMPLE 2
4-[3-[[(Cyanoimino)[[3-[4-(1,1-dimethylethyl)-1-piperidinyl]-propyl]amino]methyl]amino]phenyl]-1,4-dihydro-2,6-dimethyl-3,5-pyrazinedicarboxylic acid, dimethyl ester Following the general procedure described in Example 1, the title compound was prepared from 1,4-dihydro-2,6-dimethyl-4-(3-isothiocyanatophenyl)-3,5-pyrazinedicarboxylic acid, dimethyl ester (116 mg, 0.32 mmol) using 4-tert-butyl-piperidine-1-propanamine (77 mg, 0.39 mmol). The desired product was isolated as a yellow foam-like material (130 mg, 72%); $^1$H-NMR (CDCl$_3$) δ 7.41 (br, 1H), 7.10 (t, 1H, J=8.0 Hz), 6.60 (d, 2H, J=7.6 Hz), 6.54 (br, 1H), 5.70 (br, 1H), 3.76 (s, 6H), 3.31 (m, 2H), 3.06 (m, 2H), 2.51 (m, 2H), 2.42 (m, 6H), 2.07 (m, 2H), 1.79 (m, 2H), 1.62 (m, 2H), 1.15–1.40 (m, 2H), 1.00 (m, 1H), and 0.80 (s, 6H); $^{13}$C-NMR (CDCl$_3$) δ 166.3, 149.8, 129.9, 118.1, 116.4, 110.5, 108.5, 54.2, 51.9, 45.9, 40.1, 32.1, 27.3, 25.6, and 17.8.

Anal. Calcd. for C$_{30}$H$_{43}$N$_7$O$_4$·0.4CH$_2$Cl$_2$·0.4H$_2$O: C, 60.16; H, 7.41; N, 16.16. Found: C, 60.36; H, 7.54; N, 16.19.

EXAMPLE 3

1,4-Dihydro-2,6-dimethyl-4-[3-[[[[3-[4-(1,1-dimethylethyl)-1-piperidinyl]propyl]amino]carbonothioyl]amino]phenyl]-3,5-pyrazine dicarboxylic acid, dimethyl ester 1,4-Dihydro-2,6-dimethyl-4-(3-isothiocyanatophenyl)-3,5-pyrazinedicarboxylic acid, dimethyl ester (25 mg, 0.069 mmol) was refluxed with 4-tert-butyl-piperidine-1-propanamine (16 mg, 0.081 mmol) in 2 mL of benzene for 30 min. Chromatographic purification (silica gel, eluted with 10% (v/v) methanol in methylene chloride) of the resultant residue after concentration in vacuo gave the title compound as a yellow powder (64%); $^1$H-NMR (CDCl$_3$) δ 8.20 (br, 1H), 7.98 (br, 1H), 7.05 (t, 1H, J=8.1 Hz), 6.79 (br, 1H), 6.66 (d, 1H, J=8.0 Hz), 6.50–6.60 (m, 2H), 3.70 (s, 6H), 3.55 (m, 2H), 3.28 (m, 2H), 2.72 (m, 2H), 2.30–2.55 (m, 2H), 2.37 (s, 6H), 1.86 (m, 2H), 1.50–1.80 (m, 2H), 0.95–1.25 (m, 1H), and 0.79 (s, 6H); $^{13}$C-NMR (CDCl$_3$) δ 180.9, 166.3, 152.8, 150.1, 129.9, 116.3, 112.7, 109.9, 108.5, 53.9, 51.8, 44.9, 42.1, 32.1, 29.8, 27.2, 24.7, 24.5, and 17.8.

EXAMPLE 4

4-[3-[[[[3-[4-(3-Methoxyphenyl)-1-piperidinyl]propyl]-amino]carbonothioyl]amino]phenyl]-1,4-dihydro-2,6-dimethyl-3,5-pyrazinedicarboxylic acid, dimethyl ester 1,4-Dihydro-2,6-dimethyl-4-(3-isothiocyanatophenyl)-3,5-pyrazinedicarboxylic acid, dimethyl ester (500 mg, 1.4 mmol) was refluxed with 4-(3-methoxyphenyl)-piperidine-1-propanamine (380 mg, 1.5 mmol) in 8 mL of benzene for 2 hours. Chromatographic purification (on silica gel, 100% methylene chloride first, followed by 10% (v/v) methanol in methylene chloride) of the residue after concentration in vacuo gave the title compound as a yellow foam (807 mg, 95%); $^1$H-NMR (CDCl$_3$) δ 7.61 (br, 1H), 7.20 (t, 1H, J=7.9 Hz), 7.12 (t, 1H, J=8.1 Hz), 6.88 (br, 1H), 6.60 (m, 3H), 6.57 (dd, 1H, J=8.3, 2.1 Hz), 6.47 (br, 1H), 3.78 (s, 3H), 3.73 (s, 6H), 3.60–3.80 (m, 2H), 2.94 (m, 2H), 2.37 (s, 6H), 2.25–2.50 (m, 3H), 2.03 (m, 2H), 1.60–1.85 (m, 4H), 1.40–1.60 (m, 2H); $^{13}$C-NMR (CDCl$_3$) δ 166.0, 159.6, 152.5, 149.2, 147.7, 130.2, 129.5, 119.5, 115.8, 113.1, 112.2, 111.1, 109.7, 108.8, 63.6, 55.2, 54.2, 51.8, 42.5, 32.8, 25.4, and 18.0.

Anal. Calcd. for C$_{32}$H$_{41}$N$_5$O$_5$S·0.64CH$_2$Cl$_2$·1.31H$_2$O: C, 57.17; H, 6.60; N, 10.21. Found: C, 57.07; H, 6.19; N, 10.22.

EXAMPLE 5

4-[3-[[[[3-(4-cyclohexyl-1-piperazinyl)propyl]amino]-carbonothioyl]amino]phenyl]-1,4-dihydro-2,6-dimethyl-3,5-pyrazinedicarboxylic acid, dimethyl ester 1,4-Dihydro-2,6-dimethyl-4-(3-isothiocyanatophenyl)-3,5-pyrazinedicarboxylic acid, dimethyl ester (500 mg, 1.4 mmol) was refluxed with 4-cyclohexyl-1-piperazine-1-propanamine (345 mg, 1.5 mmol) in 8 mL of benzene for 2 hours. Chromatographic purification (on silica gel, 100% methylene chloride first, followed by 10% (v/v) methanol in methylene chloride) of the residue after concentration in vacuo gave the title compound as a yellow foam (752 mg, 92%); $^1$H-NMR (CDCl$_3$) δ 7.63 (br, 1H), 7.11 (t, 1H, J=8.0 Hz), 6.85 (br, 1H), 6.72 (br, 1H), 6.60 (d, 1H, J=8.2 Hz), 6.56 (dd, 1H, J=8.3, 2.2 Hz), 6.45 (br, 1H), 3.75 (s, 6H), 3.65 (m, 2H), 2.40 (s, 6H), 2.31 (t, 2H, J=6.6 Hz), 2.20–2.60 (m, 8H), 2.16 (m, 1H), 1.50–1.95 (m, 7H), 1.00–1.30 (m, 5H); $^{13}$C-NMR (CDCl$_3$) δ 165.9, 152.5, 149.2, 130.1, 112.0, 108.8, 63.6, 53.2, 51.9, 48.7, 29.0, 26.2, 25.8, 25.3, and 18.0.

Anal. Calcd. for C$_{30}$H$_{44}$N$_6$O$_4$S·0.58H$_2$O: C, 60.54; H, 7.65; N, 14.12. Found: C, 60.53; H, 7.64; N, 13.57.

EXAMPLE 6

4-[3-[[[[3-[4-(3-Methoxyphenyl)-1-piperidinyl]propyl]amino]-carbonyl]amino]phenyl]-1,4-dihydro-2,6-dimethyl-3,5-pyrazinedicarboxylic acid, dimethyl ester 4-(3-Aminophenyl)-1,4-dihydro-2,6-dimethyl-3,5-pyrazinedicarboxylic acid, dimethyl ester (150 mg, 0.47 mmol) was slowly added into a mixture of 1,1'-carbonyldiimidazole (117 mg, 0.72 mmol) and triethylamine (145 mg, 1.44 mmol) in 5 mL of DMF and the reaction mixture was stirred for 60 min. 4-(3-Methoxyphenyl) piperidine-1-propanamine (176 mg, 0.69 mmol) was added to the reaction mixture, and the reaction was stirred at room temperature for 30 min. DMF was removed in vacuo and the residue was purified by chromatography (on silica gel, 10% (v/v) methanol in methylene chloride then followed by 2M ammonia in methanol) to give the title compound as an orange foam (200 mg, 72%); $^1$H-NMR (CDCl$_3$) δ 7.55 (br, 1H), 7.35 (br, 1H), 7.20 (t, 1H, J=7.6 Hz), 6.92 (t, 1H, J=8.1 Hz), 6.60–6.80 (m, 4H), 6.54 (d, 1H, J=7.6 Hz), 6.32 (dd, 1H, J=8.2, 2.0 Hz), 5.99 (br, 1H), 3.77 (s, 3H), 3.71 (s, 6H), 3.16 (m, 2H), 3.03 (m, 2H), 2.46 (m, 3H), 2.29 (s, 6H), 1.95–2.20 (m, 2H), 1.60–1.90 (m, 6H); $^{13}$C-NMR (CDCl$_3$) δ 166.6, 159.7, 156.8, 151.9, 149.7, 147.4, 139.4, 129.5, 129.2, 119.3, 112.9, 111.4, 108.9, 108.5, 106.1, 56.0, 55.2, 54.1, 51.7, 42.2, 38.6, 32.8, 26.8, and 17.6.

Anal. Calcd. for C$_{32}$H$_{41}$N$_5$O$_6$·0.27CH$_2$Cl$_2$·0.51H$_2$O: C, 62.13; H, 6.88; N, 11.23. Found: C, 62.04; H, 7.06; N, 11.08.

EXAMPLE 7

4-[3-[[[[3-(4-cyclohexyl-1-piperazinyl)propyl]amino]-carbonyl]amino]phenyl]-1,4-dihydro-2,6-dimethyl-3,5-pyrazinedicarboxylic acid, dimethyl ester Following the procedure described in Example 6, the title compound was prepared from 4-(3-aminophenyl)-1,4-dihydro-2,6-dimethyl-3,5-pyrazinedicarboxylic acid, dimethyl ester (150 mg, 0.47 mmol) and 4-cyclohexyl-1-piperazine-1-propanamine (160 mg, 0.70 mmol). The desired product was isolated as an orange foam (210 mg, 78%); $^1$H-NMR (CDCl$_3$) δ 7.20 (br,1H), 7.00 (t, 1H, J=8.0 Hz), 6.87 (br, 1H), 6.68 (d, 1H, J=7.7 Hz), 6.59 (m, 1H), 6.39 (dd, 1H, J=8.1, 2.3 Hz), 3.75 (s, 6H), 3.19 (m, 2H), 2.36 (s, 6H), 2.29–2.70 (m, 10H), 2.21 (m, 1H), 1.50–1.95 (m, 7H), 0.95–1.30 (m, 5H); $^{13}$C-NMR (CDCl$_3$) δ 159.2, 108.8, 63.5, 56.4, 53.6, 49.0, 39.8, 29.0, 26.7, 26.3, 25.9, and 17.8.

Anal. Calcd. for C$_{30}$H$_{44}$N$_6$O$_5$·0.02CH$_2$Cl$_2$·0.73H$_2$O: C, 61.79; H, 7.86; N, 14.40. Found: C, 61.57; H, 8.39; N, 14.73.

What is claimed is:

1. A compound of the formula

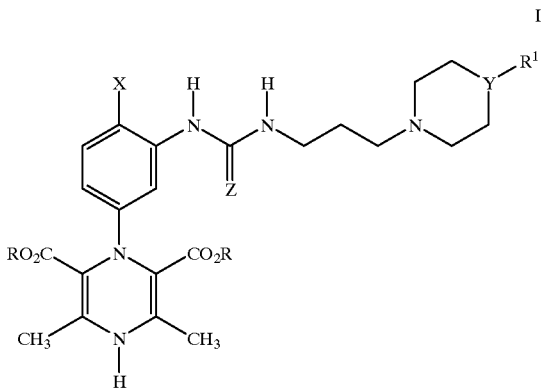

wherein
- R is $C_{1-3}$ alkyl;
- X is hydrogen or fluoro;
- Z is oxygen, sulfur, N—CN;
- Y is nitrogen or CH; and
- $R^1$ is tert-butyl, cyclohexyl, phenyl or methoxyphenyl; or a nontoxic pharmaceutically acceptable salt thereof.

2. The compound of claim 1 wherein R is methyl.

3. The compound of claim 1 wherein X is hydrogen and Y is CH.

4. The compound of claim 1 which is 4-[3-[[(cyanoimino) [[3-(4-phenyl-1-piperidinyl)propyl]amino]methyl]amino] phenyl]-1,4-dihydro-2,6-dimethyl-3,5-pyrazinedicarboxylic acid, dimethyl ester or a nontoxic pharmaceutically acceptable salt thereof.

5. The compound of claim 1 which is 4-[3-[[(cyanoimino) [[3-[4-(1,1-dimethylethyl)-1-piperidinyl]-propyl]amino] methyl]amino]phenyl]- 1,4-dihydro-2,6-dimethyl-3,5-pyrazinedicarboxylic acid, dimethyl ester or a nontoxic pharmaceutically acceptable salt thereof.

6. A method of promoting weight loss and treating eating disorders in a mammal which comprises administering to a mammalian host an anorexiant effective dose of a compound claimed in claim 1.

7. A pharmaceutical composition for use in promoting weight loss and treating eating disorders comprising an anorexiant effective amount of a compound claimed in claim 1 in combination with a pharmaceutically acceptable carrier.

* * * * *